(12) United States Patent
Utaka

(10) Patent No.: US 6,442,236 B1
(45) Date of Patent: Aug. 27, 2002

(54) X-RAY ANALYSIS

(75) Inventor: Tadashi Utaka, Neyagawa (JP)

(73) Assignee: Ourstex Co., Ltd., Osaka (JP)

( * ) Notice: Subject to any disclaimer, the term of this patent is extended or adjusted under 35 U.S.C. 154(b) by 0 days.

(21) Appl. No.: 09/704,030

(22) Filed: Nov. 1, 2000

(30) Foreign Application Priority Data

Nov. 1, 1999 (JP) .......................................... 11-310911

(51) Int. Cl.⁷ .............................................. G01N 23/00
(52) U.S. Cl. ...................................... 378/84; 378/145
(58) Field of Search ............................. 378/84, 44, 45, 378/47, 70, 82, 83, 145

(56) References Cited

U.S. PATENT DOCUMENTS 6,233,306 B1 * 5/2001 Va Sprang .................. 378/145

FOREIGN PATENT DOCUMENTS

JP 11-23797 1/1999

OTHER PUBLICATIONS

"Silicon drift detectors for high resolution room temperature X-ray spectroscopy" by Peter Lechner et al., Nuclear Instruments and Methods in Physics Research A 377 (1996) 346–354.

* cited by examiner

*Primary Examiner*—Drew A. Dunn
(74) *Attorney, Agent, or Firm*—Jordan and Hamburg LLP

(57) ABSTRACT

X-ray focusing instrument is provided with an annular analyzing element and a collimator. The analyzing element has an inner periphery. The analyzing element analyzes and reflects X-ray beams incident on the inner periphery. The collimator has a surface and total reflects X-ray beams on the surface to irradiate parallel beams toward a specimen. The collimator is placed within an internal space defined by the inner periphery of the analyzing element. The analyzing element and the collimator are arranged such that the axis of the analyzing element is substantially coincident with the axis of the collimator.

9 Claims, 3 Drawing Sheets

X-RAY ANALYSIS

BACKGROUND OF THE INVENTION

1. Field of the Invention

The present invention relates to an X-ray focusing instrument and an X-ray analysis apparatus.

2. Description of the Related Arts

Portable X-ray analysis apparatuses are required to be compact and lightweight. Hence, the apparatus structure typically tends toward simplicity, which makes it difficult to analyze light elements and trace elements.

X-ray fluorescence beam analysis belongs to the X-ray analyses. With X-ray fluorescence beam analysis, the primary X-ray beam from X-ray radiation source is irradiated at the specimen, and excites the atoms of the specimen to generate the X-ray fluorescence beam. This X-ray fluorescence beam is to be detected by the X-ray detector. Then analysis of the element of the specimen is to be made based on the result of the detection. The apparatus using cylindrical analyzing elements was suggested for this purpose (Cf. Japan Patent Laid-open Pub. No. Hei11-23797). Under this conventional technique, it is possible to analyze the specific trace elements with high sensitivity, as the primary X-ray beam, monochromatic by analyzing element, is irradiated at the specimen.

However, the above conventional technique is not appropriate to analyze the light elements, such as sodium or magnesium, for with this technique the primary X-ray beam is to become monochromatic, it has no low-energy spectrum in it.

Furthermore, though this technique intends enlargement of the area of the analyzing surface by using cylindrical analyzing elements, the area does not become large enough as expected, as the axial length effective for the analysis is too short. Hence, the strength of the monochromatic light obtained is too low; it is difficult to analyze trace heavy elements with good sensitivity.

In addition, this technique uses so-called side window type X-ray tube. In such a case, scattering electrons should be scattered from the target, which has electric potential at the earth point. Hence, if the window material (beryllium layer) is thin, it will be distorted and cracked by the heat. So, thick beryllium layer with the thickness of 0.5 mm or more is generally used as the window material. Under such condition, it becomes impossible to analyze light elements, as low-energy spectrum of the primary X-ray is to be absorbed into the window material,

SUMMARY OF THE INVENTION

The present invention was conceived to solve the above problems involved in the prior art. It is therefore the object to provide an X-ray focusing instrument and an X-ray analysis apparatus, small enough as portable apparatuses, and at the same time, appropriate for analyses of light elements and trace heavy elements.

The above object is attained by a first aspect of the present invention. The X-ray focusing instrument focuses some of X-ray beams emitted from the X-ray radiation source on the specimen. The X-ray focusing instrument is provided with an annular analyzing element and a collimator. The analyzing element has an inner periphery, which analyzes and reflects the incident X-ray beam. The collimator has a surface which reflects the X-ray beam totally and irradiates the specimen with parallel beam. The collimator is to be set in the internal space defined by the inner periphery of the analyzing element. The analyzing element and collimator are arranged so that the axis of the annular analyzing element and that of collimator can substantially coincide with each other.

To use this X-ray focusing instrument, it is necessary to place the shield member which screens the incident primary X-ray beam in the collimator or the primary X-ray emitted from the collimator on the path of the X-ray beam. This shield member should be freely inserted or removed.

In the case of analyzing heavy elements, it is required to insert the shield member on the path of the primary X-ray beam. By this process, only the monochromatic primary X-ray beam can reach the specimen. As the excitation X-ray beam does not contain the noise, it is possible to analyze trace heavy elements with good sensitivity.

In the case of analyzing light elements, it is required to remove the shield member. The X-ray beam analyzed by the analyzing element as well as the primary X-ray beam which includes the continuous X-ray focused by the collimator is to be focused on the small area of the specimen. Thus, the primary X-ray beam obtained includes low-energy spectrum, which enables analysis of light elements.

By using this X-ray focusing instrument, it becomes possible to analyze both light and trace heavy elements selectively.

In a preferred embodiment of the present invention, the inner periphery of the analyzing element is to be formed into a barrel shape curving along the axis. This barrel shape enables the enlargement of the effective area of the analyzing element by about 70 times compared to the area obtained by the conventional technique, which uses the cylindrical analyzing element. Hence, the intensity of the X-ray beam becomes 70 times larger, as well (in the case of using energy of 20 keV and lithium fluoride as the monochromator crystal). Thus, it becomes possible to analyze trace heavy elements with good sensitivity.

In another preferred embodiment of the present invention, the above analyzing element is formed in the first circular tube; the collimator is to be formed in the second cylindrical tube; and the path of the incident X-ray beam from the X-ray radiation source on the analyzing element and that of the X-ray beam emitted from the analyzing element toward the specimen is to be formed between these two tubes.

Thus, there is no need to place a slit additionally, for the path of the X-ray beam is formed between the analyzing element and the collimator, which enables the apparatus to be smaller. It is not necessary to decide the location of the slit to obtain high sensitive analyzing element.

As analyzing element monochromatic crystal such as lithium fluoride can be used, but artificial multi-layered grating can also be used.

The above object is attained by a second aspect of the present invention. The X-ray analysis apparatus makes analysis based on the detected result of the X-ray beam from the specimen. This X-ray analysis apparatus is provided with X-ray radiation source, analyzing element, collimator and X-ray detector. The X-ray radiation source radiates the primary X-ray beam. The analyzing element diffracts the primary X-ray beam from the X-ray radiation source to obtain monochromatic primary X-ray beam, and reflects the monochromatic primary X-ray beam toward the specimen. The collimator reflects the primary X-ray beam from the X-ray radiation source totally, and focuses on the specimen. The X-ray detector detects the X-ray beam from the specimen. The analyzing element is to be formed circularly having inner periphery which diffracts the primary X-ray beam. The collimator has the surface on which the primary X-ray beams are reflected totally. The collimator is placed in the internal space defined by the inner periphery of the analyzing element. The analyzing element and the collimator are so arranged that the axis of the annular analyzing element and that of the collimator can substantially coincide with each other.

The X-ray analysis apparatus, which the present invention is applied to, can make analysis of the X-ray fluorescence beam as well as diffracted X-ray beam. The analysis of the X-ray fluorescence beam is made by analyzing the element of the specimen by detecting the X-ray fluorescence beam generated from the specimen. The analysis of the diffracted X-ray beam is made to know the structure of the lattice from the angle of the diffraction of the diffracted X-ray beam.

BRIEF DESCRIPTION OF THE DRAWINGS

The present invention will be understood more apparently from the following description of the preferred embodiments in conjunction with the accompanying drawings. It is however to be appreciated that the embodiments and the drawings are for illustrative purposes only and that the scope of the present invention is defined by the appended claims. In the accompanying drawings, identical reference numerals denote the same or corresponding parts throughout several views.

DESCRIPTION OF THE PREFERRED EMBODIMENTS

A presently preferred embodiment of the present invention will now be described with reference to the accompanying drawings.

Figure 1:
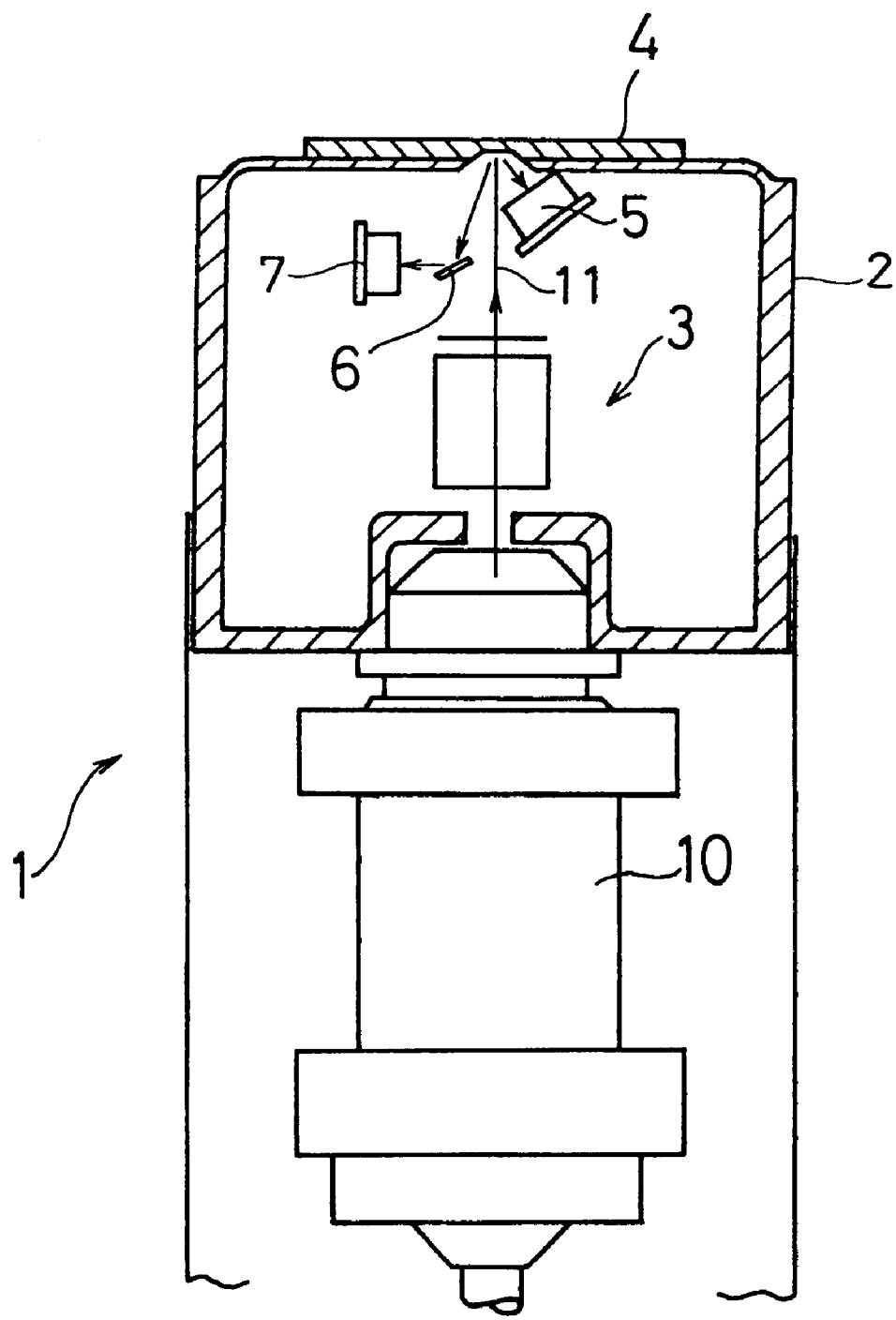
FIG. 1 is a schematic sectional view showing a measurement unit of an X-ray fluorescence beam analysis apparatus in accordance with one embodiment of the present invention.

This portable X-ray fluorescence beam analysis apparatus comprises a measurement unit 1 of FIG. 1, and a measurement controller and a personal computer (processing unit) which are not shown.

In FIG. 1, the measurement unit 1 houses the focusing instrument 3 and X-ray detector 5, mirror 6 and CCD camera 7 in an airtight case (hermetically sealed enclosure) 2. In the airtight case 2 are provided with a specimen mount 4 for the specimen. The primary X-ray beam 11 is radiated from the X-ray tube 10, which composes an X-ray radiation source, toward the specimen through X-ray focusing instrument 3. As shown in the FIG. 2, this primary X-ray beam 11 excites the atoms of the specimen 20 and causes the generation of X-ray fluorescence beam 12. This X-ray fluorescence beam 12 incident in the X-ray detector 5 is to be detected and analyzed; thus the known analysis of X-ray fluorescence beam is to be made by the personal computer.

Figure 2:
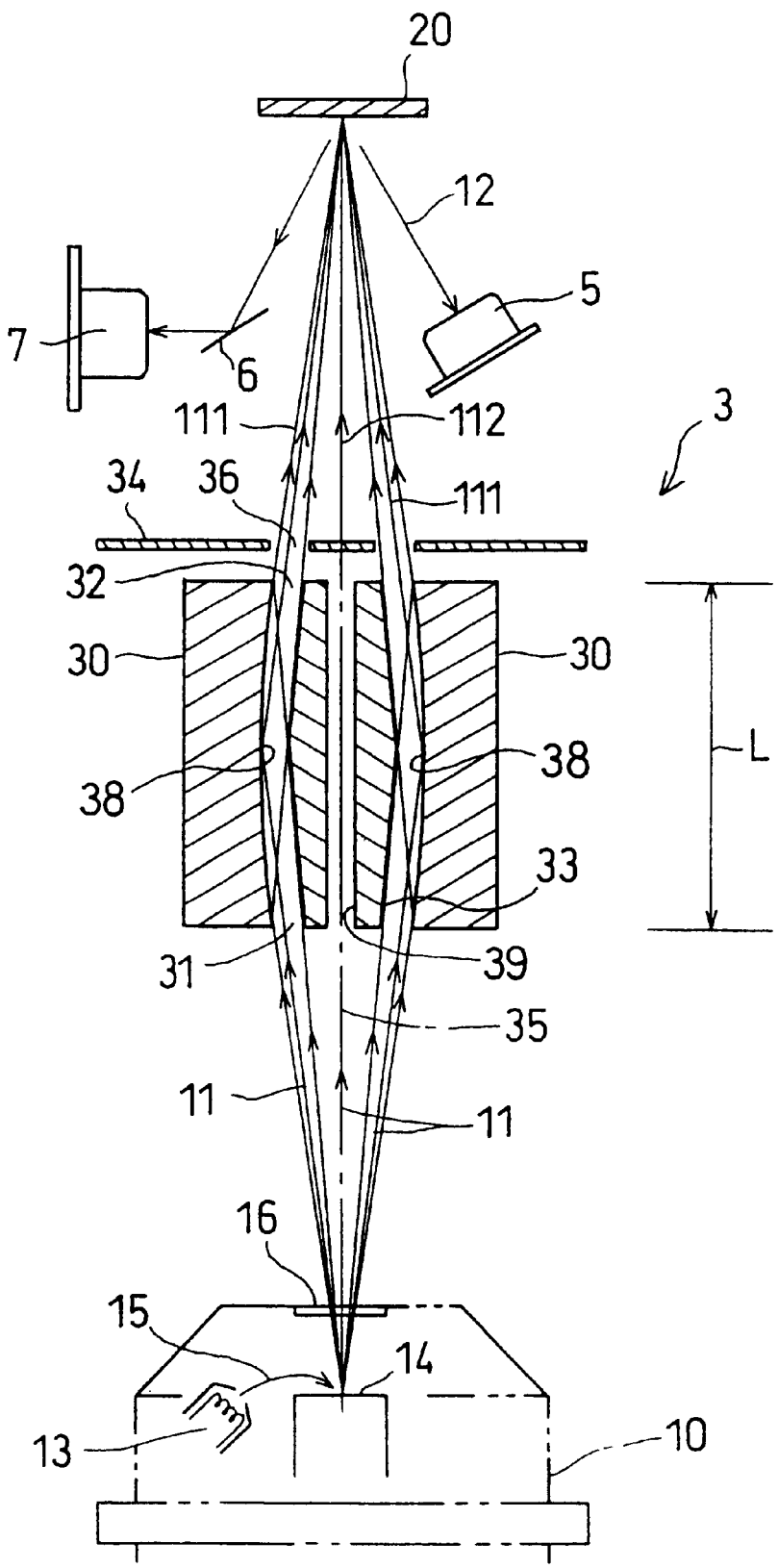
FIG. 2 shows a schematic configuration of an optical system of the measurement unit of FIG. 1.

As shown in FIG. 2, X-ray tube 10 is an end window type X-ray tube which is air-cooled. Here, filament 13 is being grounded, while voltage of plus value is added to the target 14. Thus, scattering electron is not likely generated by the collision of the electron 15 and the target 14, therefore the impairment of the beryllium layer of the window material 16 by the heat seldom occurs. That enables the window material 16 as thin as 75 μm. In this way, the low-energy spectrum of the primary X-ray beam 11 is not easily absorbed by the window material 16, thus the analysis of light elements becomes possible. Voltage of the X-ray tube 10 can be set freely by choosing the appropriate value.

The X-ray focusing instrument 3 mentioned above is placed between the specimen 20 and the X-ray tube 10. The specimen 20, the focusing instrument 3 and the X-ray tube 10 are arranged on the axis 35. The focusing instrument 3 is provided with analyzing element 30, the total reflection collimator 33 and the shielding panel (shield member) 34.

The analyzing element 30 has an inner periphery 38 which analyzes and reflects the primary X-ray beam 11; i.e., the analyzing element 30 makes Bragg's reflection only for the primary X-ray beam 11 incident at a certain angle of incidence on the inner periphery 38, thus monochromatic primary X-ray beam 111 is obtained and irradiated at the specimen 20. The analyzing element 30 is formed into a barrel shape, in which the cross section which crosses the axis 35 at a right angle is formed in a circular first tube, and the inner periphery 38 is curved along the axis 35. Thus, the inner periphery 38 is able to make Bragg's reflection for the primary X-ray beam 11 in the whole circuit around the axis 35 and in a wide range of the total length L of the analyzing element 30. Thus, the barrel-shaped inner periphery 38 enables the analyzing element 30 to focus the primary X-ray beam 111 with the specific wave length on the specimen 20 at a certain angle of incidence. As a result, the proportion of S/N of the background of the primary X-ray 111 becomes smaller.

As the curve along the axis 35, various curves, such as arc or logarithmic-spiral can be adopted (Cf. Japan Patent Laid-open Pub. Nos. Hei6-082400, Hei6-082398).

The total reflection collimator 33 is formed in a cylindrical second tube and has a surface 39, which reflects X-ray beam totally and irradiates the parallel beam on the specimen 20. The total reflection collimator 33 is placed in the internal space defined by the inner periphery 38 of the analyzing element 30. This total reflection collimator 33 is arranged on the same axis as the analyzing element 30. This total reflection collimator 33 should be preferably formed in the inside surface 39 of the narrow cylinder; otherwise, soller slits which arrange a plurality of flat panels parallel to each other can also be adopted.

The space defined between the analyzing element 30 and the total reflection collimator 33 forms the path of the primary X-ray beam 11 and 111. The lower end 31 and upper end 32 of that path provide the first and second slits, 31 and 32.

The cross sections of the first and second slits 31 and 32 are formed in a circular shape respectively, at the point where they cross the axis 35 at a right angle. The primary X-ray beam 11 incident at a certain angle of incidence toward the inner periphery 38 of the analyzing element 30 passes this first slit 31. The primary X-ray beam 111, which is reflected at a certain angle of reflection against the inner periphery 38 of the analyzing element 30, passes this second slit 32.

The shielding panel 34 mentioned above is used to limit (screen) the primary X-ray beam 112, which is radiated from the total reflection collimator 33. The shielding panel 34 is set on the path of the primary X-ray beam 111 between the focusing instrument 3 and the specimen 20, and it can be set and removed freely. The passing slot 36 enables the passing of the primary X-ray beam 111, which is analyzed by the analyzing element 30. It is preferable that the shielding panel 34 is rotated by a drive like a motor. The shielding panel 34 may screen the primary X-ray beam 11, which is radiated from X-ray tube 10 toward the total reflection collimator 33.

Figure 3A:
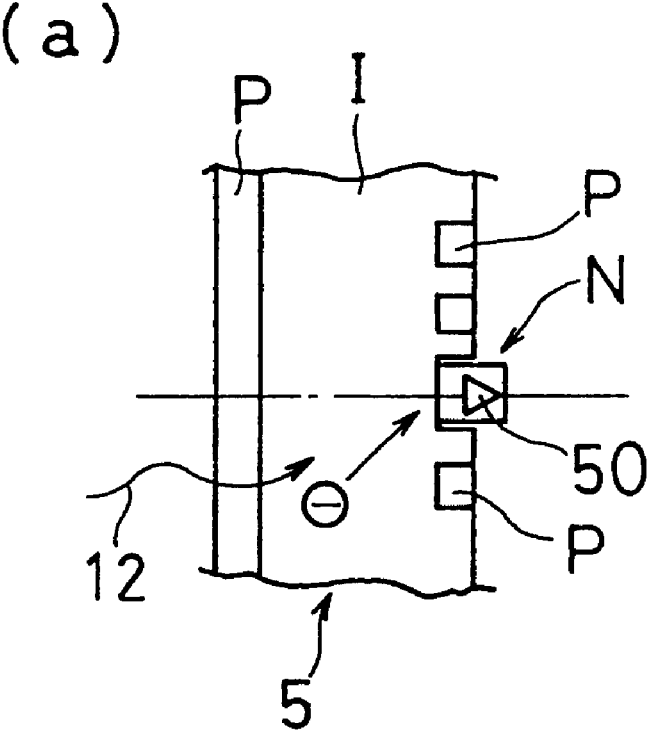
FIGS. 3(a) and (b) show a concept of a silicon drift type detector and of an Si-PIN type detector, respectively.

The X-ray detector 5 is a so-called silicon drift type detector [cf. NUCLEAR INSTRUMENTS and METHODS IN PHYSICS RESEARCH A 377 (1966) pp. 346–351], and as shown in FIG. 3(a), a plurality of P layers are embedded in the I layer forming a concentric circle, and FET (electric field effect transistor) 50 for output is embedded in the N layer, a central anode. This X-ray detector 5 has the higher voltage the nearer it comes to the anode. Therefore, electrons generated from the incidence of X-ray fluorescence beam 12 focuses on N layer. As it is amplified by FET 50 (preamplifier) embedded in N layer, there is no possibility of being trespassed by noises before amplification, which enables the higher resolving power of the spectrum.

This X-ray detector 5 of this embodiment should preferably be cooled twice by Pertier element. The X-ray detector 5 enables the generation of energy resolution with 150 eV and low-energy part will be clear. This X-ray detector 5 uses beryllium layer with 8 $\mu$m for the window material, which enables analysis of light elements such as fluorine.

The CCD camera 7 in FIG. 2 is used to confirm the location of the specimen 20. The picture taken will be displayed on the monitor of the personal computer. The airtight case 2 in FIG. 1 is a pressure resistant container; it can, for example, keep the inside chamber vacuum or helium atmosphere. In this way, it avoids the absorption of X-ray beam by vapor and enables analysis of light elements with smaller atomic number, such as fluorine.

Use of this apparatus will be described.

In the case of analyzing heavy elements in the specimen 20, it is necessary to set the shielding panel 34 on the path of X-ray beam 111 of the FIG. 2, and at the same time, set the voltage of X-ray tube 10 to 50 kV, and use high-energy K$\alpha$ ray beam from the target 14 as characteristic X-ray beam. In this case, the primary X-ray beam 112 which passes the total reflection collimator 33 is limited (screened) by shielding panel 34. On the other hand, the primary X-ray (characteristic X-ray) 111 monochromated by analyzing element 30 passes the passing hole 36 and is radiated at the specimen 20. Then the X-ray fluorescence beam 12 from the specimen 20 is detected by the X-ray detector 5. Thus, high-energy monochromatic X-ray beam excites the specimen 20, it is possible to analyze heavy elements with good sensitivity.

In the case of analyzing light elements contained in the specimen 20, it is required to remove the shielding panel 34 from the path of the primary X-ray beam 111 and set the voltage of X-ray tube 10 under 20 kV, and use low-energy X-ray beam of L-series from target 14 as excitation source. In this case, the primary X-ray beam 111 monochromated by analyzing element 30 and the primary X-ray beam 112 which passes the total reflection collimator 33 are to be radiated at the specimen 20, then X-ray fluorescence beam 12 from the specimen 20 will be detected by the X-ray detector 5. In this case only the components of low-energy L beam is radiated from the X-ray tube 10, so the intension of continuous X-ray beam also is to be low. Thus, only L-beams of low-energy component excite the specimen 20, it becomes possible to analyze light elements.

Figure 3B:
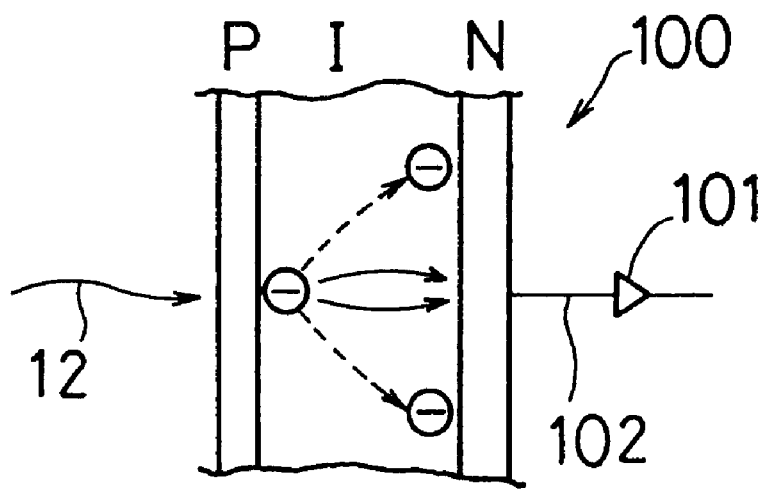

In the present invention Si-PIN diode type X-ray detector 100 shown in the FIG. 3(b) can also be used. However, as wiring material 102 is inserted between N layer and amplifier 101 in this X-ray detector 100, this material becomes the noise source. The generated electrons which disperse as shown by a broken line also cause the declining of the resolving power. Thus, using this X-ray detector 100, it is only possible to analyze light elements up to aluminum. Therefore, the preferable X-ray detector must be the silicon drift type X-ray detector 5.

Although the preferred embodiments have been described hereinabove with reference to the accompanying drawings, it would be easy for those skilled in the art to conceive various changes and modifications within the obvious scope from this specification without departing from the spirit of the present invention.

For example, the fixed location of the analyzing element can allow a slight adjustment relative to the airtight case. The angle of the inclination in the three-axial directions of the analyzing element may also allow the slight adjustment.

Therefore, such changes and modifications are to be construed as being within the scope of the present invention defined by the appended claims.

What is claimed is:

1. An X-ray focusing instrument for focusing some of X-ray beams radiated from an X-ray radiation source on a specimen, the instrument comprising:

an annular analyzing element having an inner periphery, the element analyzing X-ray beams incident on said inner periphery to obtain monochromatic X-ray beams, for reflection toward said specimen; and a collimator having a surface and reflecting X-ray beams totally on said surface to irradiate parallel beams onto said specimen;

said collimator being disposed in an internal space defined by said inner periphery of said analyzing element, said annular analyzing element and said collimator being arranged in such a manner that the axis of said analyzing element is substantially coincident with the axis of said collimator.

2. The X-ray focusing instrument according to claim 1, wherein said inner periphery of said analyzing element curves along said axis so that said inner periphery is shaped into a barrel.

3. The X-ray focusing instrument according to claim 1, wherein said analyzing element is formed of an annular, first tube and said collimator is formed of a cylindrical, second tube, and wherein between said two tubes there extends a path for X-ray beams from said X-ray radiation source incident on said analyzing element and for X-ray beams from said analyzing element toward said specimen.

4. An X-ray analysis apparatus for detecting and analyzing X-ray beams from a specimen, the apparatus comprising:

an X-ray radiation source radiating primary X-ray beams;

an analyzing element diffracting said primary X-ray beams from said X-ray radiation source to obtain monochromatic primary X-ray beams, for reflection toward said specimen;

a collimator reflecting said primary X-ray beams totally from said X-ray radiation source, for focusing on said specimen; and an X-ray detector detecting X-ray beams from said specimen;

said analyzing element being of an annular shape having an inner periphery for diffracting said primary X-ray beams, said collimator having a surface for reflecting said primary X-ray beams totally, said collimator being disposed in an internal space defined by said inner periphery of said analyzing element, said analyzing element and said collimator being arranged such that the axis of said annular analyzing element is substantially coincident with the axis of said collimator.

5. The X-ray analysis apparatus according to claim 4, further comprising:

a shield member screening primary X-ray beams incident on said collimator or primary X-ray beams radiated from said collimator, said shield member being disposed on a path for said primary X-ray beams in such a manner as to allow free insertion and removal thereof.

6. The X-ray analysis apparatus according to claim 4, further comprising:

a specimen mount for mounting said specimen thereon, said specimen mount and said X-ray radiation source being arranged on said axis, with said analyzing element and said collimator being interposed between said specimen mount and said X-ray radiation source.

7. The X-ray analysis apparatus according to claim 4, wherein said X-ray radiation source is formed of an X-ray tube, said X-ray tube including a target having a positive voltage applied thereto and a grounded filament.

8. The X-ray analysis apparatus according to claim 4, wherein said X-ray detector includes an I layer, a plurality of P layers embedded in said I layer concentrically with one another, and a preamplifier embedded at the center of concentric circles defined by said plurality of P layers in said I layer.

9. The X-ray analysis apparatus according to claim 4, further comprising:

a hermetically sealed enclosure accommodating therein said analyzing element, said collimator and said X-ray detector.

* * * * *